United States Patent [19]

Blume et al.

[11] 4,444,769

[45] Apr. 24, 1984

[54] ANTIHYPERTENSIVE DIURETIC COMBINATION COMPOSITION AND ASSOCIATED METHOD

[75] Inventors: Cheryl D. Blume; Paul H. Bonner, both of Morgantown, W. Va.

[73] Assignee: Mylan Pharmaceuticals, Inc., Morgantown, W. Va.

[21] Appl. No.: 456,311

[22] Filed: Jan. 6, 1983

Related U.S. Application Data

[63] Continuation-in-part of Ser. No. 402,279, Jul. 27, 1982, abandoned.

[51] Int. Cl.$^3$ .................... A61K 31/505; A61K 31/54
[52] U.S. Cl. ..................................... 424/246; 424/251; 424/20; 424/361; 264/109; 264/113; 264/118
[58] Field of Search ................................ 424/251, 246

[56] References Cited

U.S. PATENT DOCUMENTS 3,081,230  3/1963  Weinstock et al. ................. 424/246

OTHER PUBLICATIONS

Marvola et al., Chem. Abs. 96:91566k.
Reyes et al., Chem. Abs. 97:174735m.
Roehm, Pharma. Chem. Abs. 89:30766j.

*Primary Examiner*—Jane T. Fan
*Attorney, Agent, or Firm*—Cushman, Darby & Cushman

[57] ABSTRACT

A novel combination pharmaceutical composition is described, together with a method for making the same, wherein the pharmaceutically active ingredients are separately milled and then formed into separate granules, and only thereafter blended together to form the combination composition. The method for achieving this novel combination composition is also described. In particular, a novel combination composition of triamterene and hydrochlorothiazide having improved bioavailability and novel effectiveness to prevent or eliminate hypokalemic side effects is also described.

12 Claims, No Drawings

ANTIHYPERTENSIVE DIURETIC COMBINATION COMPOSITION AND ASSOCIATED METHOD

This application is a continuation-in-part of co-pending application Ser. No. 402,279, filed July 27, 1982, abandoned.

FIELD OF THE INVENTION

This invention relates to a novel pharmaceutical composition having effective combined diuretic and antihypertensive properties while also being capable of resisting or reversing hypokalemia. More specifically, this invention provides a novel pharmaceutical composition containing hydrochlorothiazide (6-chloro-3,4-dihydro-2H-1,2,4-benzothiadiazide-7-sulfonamide-1,1-dioxide) and triamterene (2,4,7-triamino-6-phenylpteridine), and exhibiting enhanced bioavailability of both ingredients. Also an improved novel method for using and administering a diuretic and antihypertensive combination medication with prevention or elimination of hypokalemic side effects is provided. This invention further provides a novel method for generally making pharmaceutical compositions composed of two or more active ingredients which differ significantly from each other in their relative hydrophobic and/or hydrophilic characteristics and/or physiological fluid solubilities.

DESCRIPTION OF THE PRIOR ART

The preparation of pharmaceutical compositions having two or more active ingredients has been and is a common requirement in medicine. Frequently, ingredients may be simply combined without difficulties pertaining to stability or bioavailability. In other instances, the respective active ingredients have the capability of interacting with each other, introducing stability problems even in solid preparations, which then require special preparatory measures. In other instances, care must be taken to ensure that the bioavailability of the active ingredients in combination pharmaceutical preparations is not adversely affected by each other by the various pharmaceutically acceptable but inert components which typically must be included in the composition when formulated into tablet or capsule form.

The present invention is concerned with pharmaceutical preparations having at least two active ingredients, at least one of which is sparingly soluble in aqueous physiological fluids, and which also significantly differ from each other in their respective hydrophobicities or hydrophilicities. In such compositions, the active ingredient must typically be made available in very finely divided form to provide maximum surface area in order to aid the dissolution thereof in the physiological fluids. However, when one of the ingredients has hydrophobic characteristics, it appears that the fine particles of that ingredient will tend to cover the surface of the finely divided particles of a second, relatively hydrophilic ingredient, and thus significantly depress the ability of the latter ingredient to enter into solution in the body fluid.

Indeed, it is sometimes the case that the relatively hydrophobic ingredient must be used in a relatively greater weight amount than the relatively hydrophilic ingredient, and thus statistically the hydrophilic particles will very significantly tend to be coated or covered by the greater number of fine hydrophobic particles, in a kind of small agglomerate particle formed during tableting or granulation procedures employed for making up a individual dose formulation, particularly in either tablet or capsule form. The result is that the bioavailability of the hydrophilic material is adversely affected, depressed, and the formulations exhibit erratic behavior in terms of the amount of medication actually received by the patient. This can cause grave difficulties in the treatment of serious illnesses. At times, also, the hydrophobic material itself in such compositions is also only erratically bioavailable.

In any event, in such compositions the pharmacological goals are to make each of the ingredients maximally bioavailable, at the lowest administered dose level possible, and preferably in a single tablet or capsule (rather than multiple tablets or capsules). Further, the formulation should also be such that the bioavailability level of the ingredients should be desirably uniform, i.e. with a relatively low coefficient of variation when multiple patient responses are statistically analyzed.

A case in point illustrating these problems and, relating to one embodiment for the practice of this invention, is the antihypertensive medication combination of hydrochlorothiazide and triamterene.

Hydrochlorothiazide is a known single entity pharmaceutical for administration to human patients in order to provide diuretic and antihypertensive medication and treatment. In addition to producing beneficial effects on hypertension, the diuretic action serves to relieve edema caused by renal, cardiac, hepatic ineffectiveness or other causes.

However, one of the problems which arises when thus administering single-entity hydrochlorothiazide is that this medication also tends to cause a loss of potassium from the patient, which may be excessive, and which may thereby create an undesired hypokalemic condition. Among the undesired results of hypokalemia in the patient are muscle weakness, general fatigue and an exaggeration of the cardiac responses to various drugs which may also be administered to the patient. While potassium supplements have been prescribed, this may cause further adverse side effects such as gastrointestinal tract lesions, forming a site for possible ulceration and possible perforation, etc.

It has also been known to administer hydrochlorothiazide in combination with the administration of triamterene. The latter compound has the capability of resisting hypokalemia by retarding the discharge of potassium from the patient's body. Description of such prior activities are found in U.S. Pat. No. 3,081,230; "Maintenance of Potassium Balance During Diuretic Therapy" by Kohvakka et al. 205 Acta Med Scand, Vol. 205, pages 319-324 (1979) and "The Influence of Dosage Form on the Activity of a Diuretic Agent", by Tannenbaum et al., Clinical Pharmacology and Therapeutics, Volume 9, No. 5, pp. 598-604 (1968). Typically such prior art unit dosage forms have been prepared with an intimate mixing together of all of the various, finely divided, components.

However, one of the problems which has continued to exist with such combinations as previously provided in the art is that the combined compositions have been only erratically and incompletely absorbed in patients, and have provided only relatively low bioavailability of the components, which has in turn obscured or increased the apparent amount of triamterene required by a patient.

Another problem which has been encountered has been the risk of loss of effective control of hypertension or edema when a patient under treatment with an optimally bioavailable single entity hydrochlorothiazide is subsequently transferred to a triamterene-hydrochlorothiazide combination to attempt to control hypokalemia. A previously acceptable and effective dose level of hydrochlorothiazide may now be relatively inadequate due to depressed bioavailability. Moreover, there has not been experienced effective control or reversal of hypokalemia. While it might be thought that such difficulties could be surmounted by administering liquid suspensions, or separate solid dose levels of the active ingredients in separate tablets or capsules, such approaches are in general undesired because, inter alia, of problems of patient compliance in taking the proper prescribed medication level at all times.

Thus, while the properties and medicinal benefits of hydrochlorothiazide have long been known, as well as those of triamterene, as well as the expected benefits to arise from administering a combination of the two together, there has remained a need for a pharmaceutical composition combining these two materials in such a manner that each ingredient is optimally bioavailable with enhanced safety and pharmaceutical effectiveness. Specifically there has remained a need for a single, solid-form dosage unit composition containing both hydrochlorothiazide and triamterene, with combined diuretic and antihypertensive properties, while also exhibiting a bioavailability of the active ingredients as least about comparable to that of the single dosage hydrochlorothiazide and/or triamterene and which will also resist or reverse hydrochlorothiazide-induced hypokalemia while using the minimum relative amount of triamterene.

GENERAL SUMMARY OF THE INVENTION

The present invention provides, in a presently preferred embodiment, a pharmaceutical composition containing both hydrochlorothiazide and triamterene, particularly in solid dosage form, whth the characteristics and properties of optimal bioavailability, with more uniform absorption of both ingredients, which permits optimal effective diuretic and antihypertensive activity while resisting or reversing hypokalemia at a minimized dose levels of triamterene.

It is therefore an object of the present invention to provide a safe and effective pharmaceutical composition combining hydrochlorothiazide and triamterene and which is adapted to serve as an antihypertensive and diuretic agent while resisting or reversing undesired hypokalemic side effects.

An additional object of this invention is to provide a method for manufacturing pharmaceutical compositions, and the resulting compositions, having at least two active ingredients, at least one of which is sparingly soluble in physiological fluids, and of significantly different hydrophobic and/or hydrophilic characteristics, wherein the resulting composition exhibits enhanced bioavailability of the medication and of increased uniformity of behavior in physiological absorption.

A further specific object of the present invention is to provide a method of manufacturing such a pharmaceutical composition, composed of hydrochlorothiazide and triamterene, the resultant pharmaceutical, and its method of use, being such that the active ingredients of the composition will be uniformly absorbed and provide high bioavailability which is comparable to that provided by a single-entity hydrochlorothiazide medication or single entity triamterene.

It is yet another object of this invention to provide such a composition and associated method which will permit resistance to or reversal of hydrochlorothiazide-induced hypokalemia while employing a minimum amount of triamterene in combination therewith.

In general, the prime specific objective of the invention is to provide a composition employing a minimum dosage of triamterene, while producing effective bioavailability and avoiding or reducing or reversing hydrochlorothiazide-induced hypokalemia. In general, hypokalemia may be considered to exist at a serum potassium level of about equal to or less than 3.5 mEq/L.

These and other objects of the invention will become apparent from the following detailed description.

DESCRIPTION OF THE PREFERRED EMBODIMENTS

In a preferred embodiment of the present invention, hydrochlorothiazide (6-chloro 3,4-dihydro-2H-1,2,4-benzothiadiazine-7-sulfonamide 1,1-dioxide) is combined with triamterene (2,4,7-triamino-6-phenylpteridine), and non-toxic pharmaceutically acceptable carriers or other materials to produce the desired pharmaceutical action.

A preferred embodiment for the method of manufacturing the pharmaceutical composition of the present invention involves the steps of providing respective quantities of triamterene and hydrochlorothiazide at a weight ratio of triamterene to hydrochlorothiazide of about 1.75 to 1.25:1. These ingredients are separately admixed with certain additional carrier materials which contribute to their enhanced bioavailability. The separate mixtures, after granulation, are then combined. The pharmaceutical composition which results is preferably provided in solid dosage form, particularly as a tablet, or alternatively as a capsule.

The quantity of triamterene, on a weight basis, should be in the range of about 1.75 to 1.25 times the quantity of hydrochlorothiazide and advantageously and most preferably about 1.5:1. As used hereinafter the expression "triamterene weight base" shall refer to the ratio of the amount on a weight basis of another component to the amount of triamterene.

The triamterene ingredient itself, in finely divided milled form, preferably such that at least about 95% pass through a 200 mesh screen, may be made up in a first mixture containing about 25 to 75 percent (on a triamterene weight basis) of a wicking agent, such as powdered cellulose, N.F., $(C_6H_{10}O_5)_n$ and preferably about 35 to 55 percent. A suitable wicking agent is that sold under the trade designation REXCEL by E. Mendell Co., (now named SOLKA-FLOC BW-100) or that sold under the trade designation EX-CEL by Sitco Chemical. Such a wicking agent should be effective to induct water to within the subsequently formed granules (see below) to swell and otherwise aid in the fragmentation of the same when exposed to aqueous physiological fluid. It is preferred that this material have a longitudinal dimension greater than would pass through a screen of about 200 mesh, in order to enhance its wicking action in the composition.

Also added to this mixture is about 20 to 240 percent (on a triamterene weight basis) percent and preferably about 150 to 190 percent of a finely-divided binder-disintegrant, such as microcrystalline cellulose, N.F. $(C_6H_{10}O_5)_n$. A suitable binder-disintegrant is that sold under the trade designation AVICEL PH-102 by FMC Corporation. A suitable wetting agent such as sodium lauryl sulfate [dodecyl sodium sulfate [$CH_3(CH_2)_{10}CH_2OSO_3Na$] may also be added in quantities of about 2 to 10 percent on a triamterene weight basis and preferably about 4 to 7 percent. A suitable material is that sold under the trade designation "Maprofix" (Onyx Chemical Co.).

Other additional non-toxic pharmaceutically-acceptable but inactive carrier materials may also be present and all of these components are admixed together to create a first mixture. Among the additional components which may be included in such first mixture as pharmaceutically inactive materials, all in finely-divided form, may be a disintegrant such as croscarmellose sodium, N.F., (a cross linked sodium carboxymethyl cellulose material), in quantities of about 6 to 22 percent on a triamterene weight basis and preferably about 10 to 18 percent. Suitable materials are those sold under the trade designations "Ac-Di-Sol" (FMC Corporation) and CLD (Buckeye Cellulose Corp.).

Also added to this first mixture is a dosage lubricant, such as magnesium stearate/sodium lauryl sulfate, prepared by providing ninety-four parts, on a weight basis, of the former and six parts of the latter, preferably initally wet-mixed and then dried and milled, in quantities of about 3 to 12 percent on a triamterene weight basis and preferably about 6 to 10 percent. (This mixture may, for instance, consist of 94 parts magnesium stearate, N.F. (Octadecanoic acid magnesium salt mg ($C_{18}H_{35}O_2$)$_2$ and 6 parts of sodium lauryl sulfate, N.F. (dodecyl sodium sulfate, [($CH_3(CH_2)_{10}CH_2OSO_3Na$]). A suitable lubricant of this type is that which has been marketed under the trade designation "Stear-O-Wet M". Additionally, a suitable flow enhancer, such as colloidal silicon dioxide, N.F., may be provided in quantities of about 1 to 5 percent on a triamterene weight basis and preferably about 2.5 to 4 percent. Suitable materials are those sold under the trade designations "Cab-O-Sil", (Cabot Corporation) and "Aerosil", (Degussa, Inc.).

As now used hereinafter the expression "hydrochlorothiazide weight basis" shall refer to the ratio of the amount on a weight basis of another ingredient to the amount of hydrochlorothiazide.

A second mixture is made up by mixing finely divided hydrochlorothiazide, preferably such that at least 95% passes through a 100 mesh screen, with about 120 to 240 percent (on hydrochlorothiazide weight basis) of a suitable binder-disintegrant such as the microcrystalline cellulose, N.F. (described above) and preferably about 160 to 200 percent; plus about 4 to 16 percent on a hydrochlorothiazide weight basis of a disintegrant, such as the croscarmellose sodium, N.F. (described above) and preferably about 10 to 12 percent; plus flow enhancer, such as colloidal silicon dioxide, N.F. ($SiO_2$) in quantities of about 0.5 to 4 percent on a hydrochlorothiazide weight basis and preferably about 1 to 3 percent; plus a lubricant such as magnesium stearate/sodium lauryl sulfate (94/6) in quantities of about 0.5 to 4 percent on a hydrochlorothiazide weight basis and preferably about 1 to 3 percent. Suitable flow enhancers include those sold under the trade designations "Cab-O-Sil" (Cabot Corporation) and "Aerosil", (Degussa).

Each of these two separately prepared mixtures of the respective active ingredients and carrier materials is thoroughly mixed and further milled if desired to optimum particle size for effective pharmaceutical use.

Each of these two mixtures is next separately compacted or compressed for the purpose of making granules of each mixture. The separate compaction steps form compressed material composites of the respective mixtures, for instance in large disk or sheet form such that the individual active ingredient particles are now in intimate physical, substantially homogeneous, admixture with the above mentioned additive material particles.

Next, the compacted materials are separately subjected to a comminuting operation to divide the same into a granulated form, whereby the respective granules of each mixture will be composed of the respective active ingredient and the above-mentioned various additives. The granules thus-formed from the compactions should have adequate structural integrity to continue to exist as finite entities in the following operations.

In a preferred form of the practice of the present invention, in separate processing of each of the two mixtures they are preferably passed through a Fitzmill, No. 00 screen, and after they have been separately compacted, they are comminuted to form respective granules of the separate mixtures with the granulated materials being passed through a Fitzmill No. 2 screen for capsules or a Fitzmill No. 2A for tablets. Other equipment of comparable function may of course be used for these purposes.

The thus-formed granules should have a size range from not more than 5% being larger than 2 mm to not more than 20% being smaller than 0.075 mm, preferably with not more than 5% having a dimension exceeding 1.5 mm, especially when a capsule is to be made.

Thereafter the thus-formed granules of the first and second mixtures are blended together to create a third, now combined, mixture. In a preferred form of the practice of this invention, a further quantity of lubricant, such as a mixture (preferably made up wet, dried and milled) of magnesium stearate/sodium lauryl sulfate (e.g. 94/6 weight ratio) is admixed in the third mixture. This may be about 0.2 to 1.0 percent of the total blended weight of the two mixtures and preferably about 0.4 to 0.7 percent. When the combined composition is ultimately formulated in capsules suitable stabilizers, surfactants and antimicrobial agents may be present. If instead a tablet is to be made, a coloring agent may be added, such as D&C yellow #10 aluminum lake in suitable coloring amount, as desired.

The combined granulated and blended mixture composition then produced by the above-described method may now be formulated into unit dosage form, e.g. as a tablet or as a capsule.

In a preferred form of the practice of the invention, the ultimate unit dosage form of the combined mixture may include hydrochlorothiazide in quantities of about 25 milligrams to 100 milligrams and desirably such that the combined weight of the active pharmaceutical ingredients, i.e., hydrochlorothiazide and triamterene, will be about 62.5 milligrams to 250 milligrams total. For example, at a weight ratio of 1.5:1, the unit dosage breakdown of triamterene to hydrochlorothiazide might be 37.5/25 mg, 75/50 mg. or 150/100 mg. It has been found that a very effective weight ratio is 75/50. In general, it will be desirable to limit the amount of the total patient consumption of triamterene per day to no more than about 150 milligrams and of hydrochlorothiazide per day to no more than about 100 milligrams. (As used herein, the term "patient" shall refer to members of the animal kingdom, including human beings.)

One of the key features of the present invention which contributes to the high bioavailability centers around the ability of said resulting unit dosage forms of this combined composition to disintegrate rapidly in the presence of physiological fluids into pre-formed separate granules, and subsequently the ability of the respective individual granules to break up rapidly in such fluids into their much smaller particulate components. This is accomplished by specific control of relative particle sizes, the blending of hydrophobic and hydrophilic materials, only after they have been separately granulated, and in a preferred embodiment, the use of wicking material, particularly with the hydrophobic component.

In general, with two exceptions, in the preferred practice of the invention most of the starting materials incorporated into the first and second mixtures will have a particle size of about 95% passing through a 200 mesh screen. In order to provide effective wicking action (to cause moisture to penetrate to the dosage unit interior), the wicking agent should have a longitudinal dimension greater than would pass through a 200 mesh screen. The (relatively hydrophilic) hydrochlorothiazide particles should also pass 95% through a 200 mesh screen, but passing about 95% through a 100 mesh screen is also acceptable. The particle size of the ingredients and carriers in the separately formed mixtures should be substantially smaller than the size of the subsequently formed granules by at least one or more orders of magnitude.

Of the active ingredients, hydrochlorothiazide, is relatively hydrophilic, while triamterene is relatively hydrophobic. As described above, it is believed that one of the problems encountered with the prior art materials and compositions has been the rather uniform presence of fine particles of triamterene on the surface of the solid dosage form (and also of agglomerates therein), thus creating a hydrophobic barrier to passage of moisture therethrough. This phenomenon evidently occurred because of the blending together of the two active ingredients, and the other conventional tableting or encapsuling additives, all in finely divided form without preliminary separate composition and granulation thereof. Moisture thus fails or is inhibited from coming in contact with the hydrochlorothiazide. This has resulted in a failure of the dosage form to disintegrate rapidly and, as a result, such compositions exhibit limited and erratic bioavailability.

By contrast, in the present invention, the separate initial granulation of the active ingredients with other materials prior to admixture and blending of the active ingredients together serves to separate the hydrophobic and hydrophilic particulate materials from each other thereby also avoiding such surface effect, and thus also facilitating disintegration of the solid dosage form into preformed granules, which are themselves also able to disintegrate rapidly to disperse the fine particles of the active ingredients. This effect is further enhanced by the increased exposed surface area of the respective ground granulated particles, which in turn increases the rate of solution.

As shown below, the dissolution and bioavailability of the triamterene ingredient is also enhanced when present in the granular form of this invention.

It will also be appreciated that this method forms separate granules which are themselves essentially homogenous, with each other, of the respective components, but that in the final composition, a heterogeneity is present in that the different granules are now blended together. Further, different formulating additives may be employed with the different active ingredients, as desired, to enhance the ultimate dissolution thereof while avoiding incompability problems.

By "granularly-heterogenous" there is meant herein the existence of individually distinct granules, one set of such granules containing the triamterene component and the other set of granules containing the hydrochlorothiazide. The term is thus inapposite with respect to a composition in which the respective granules were initially formed containing both the triamterene and the hydrochlorothiazide. The term "granularly heterogenous" continues to be apposite to the invention even when the initial individual granules, after being blended together, may be again compressed, compacted, or slugged, together to form composite larger granules for tableting, encapsulating, or the like.

A second stage of increasing bioavailability involves physiological fragmenting the separate pre-formed granules into their still smaller components. By using a wicking agent, moisture is drawn into, and swells, the interior of such granules. Also, the disintegrants and the surfactant contribute to such desired fragmentation.

It will be appreciated that one of the advantageous aspects of this embodiment of the present invention is the ability to achieve resistance to or even reversal of hydrochlorothiazide-induced hypokalemia through the action of the triamterene, as a result of the high bioavailability levels for this material being achieved by the use of finely-divided particle sizes of the active ingredients combined with independent mixing of each active ingredient with the above-described pharmaceutical carrier materials to create the separate granules. The hydrophobic triamterene granules are preferably provided with a wicking agent to assist with fragmentation of such granules. The hydrophilic hydrochlorothiazide granules, whether in a tablet or capsule form of the present invention also readily absorb water or other body fluids and facilitate prompt fragmentation of the solid dosage form into granules. The granules preferably assisted by disintegrants, a wetting agent and a wicking agent in the triameterene granules, are then broken up.

The following examples and data will further illustrate the method and a composition of the present invention.

EXAMPLE 1

To prepare 50 kilograms of the pharmaceutical composition of the present invention, at a ratio of triamterene to hydrochlorothiazide of 1.5:1 on a weight basis, the following procedure is employed.

The first mixture is made up to contain about 9.38 kilograms of triamterene, U.S.P., 4.75 kilograms of a wicking agent, 15.6 kilograms of a binder-disintegrant, 1.25 kilograms of a disintegrant, 500 grams of a wetting agent or surfactant such as sodium lauryl sulfate, 750 grams magnesium stearate/sodium lauryl sulfate (94/6) and 250 grams of a flow enhancer.

The disintegrant, magnesium stearate/sodium lauryl sulfate (94/6) and flow enhancer components are thoroughly premixed. This pre-mix is then passed through a 30 mesh screen. The triamterene, binder-disintegrant and wicking agent components are passed through a screen. All of the ingredients are then placed in a five cubic foot V-blender and blended for about 15 minutes. The mixed material is then passed through a Fitzmill No. 00 screen, high speed, impact forward, and the thus-milled mixture is subsequently slugged or compacted to create granules of the first mixture. The slugging or compacting may either form hard discs of about ¼" diameter or sheets of about ¼" thickness, etc., achieved by using about 2 to 4 tons per square inch of pressure. This compressed material is then passed through a Fitzmill No. 2A screen, medium speed, knives forward to form comminuted granules. In the event it is desired to make a capsule, a Fitzmill No. 2 screen may be substituted in this final step of preparing the granulated first mixture.

The second mixture is made by mixing together about 6.25 kilograms of finely-divided hydrochlorothiazide, U.S.P., 10.00 kilograms of a binder-disintegrant, 625 grams of a disintegrant, 125 grams of a flow enhancer and 125 grams of magnesium stearate/sodium lauryl sulfate (94/6). If a tablet is to be made, about 125 grams of a coloring agent may be added. The disintegrant, magnesium stearate/sodium lauryl sulfate and flow enhancer (along with any coloring agent used) may be pre-mixed and first passed through a 30 mesh screen. The hydrochlorothiazide and binder-disintegrant may previously be passed through an 18 or 30 mesh screen to remove any lumps. The subsequent mixing, milling, granulating procedure employed may be identical to that employed with the first mixture.

The comminuted granulated mixtures thus made separately by the above-described parallel granulation of each separate mixture may be next separately milled to an approximate granular size range of from about not more than about 5% being greater than 2 mm in length (the maximum dimension) to not more than about 20% being smaller than 0.075 mm in length.

Next, magnesium stearate/sodium lauryl sulfate, in a quantity of 250 grams, and mixed at a ratio of 94:6 on a weight basis, is passed through a 30 mesh screen. The two groups of first and second granules composed of the separate first and second mixtures are next admixed and blended together with the magnesium stearate/sodium lauryl sulfate in a five cubic foot V-blender for about 15 minutes.

When a tablet is desired, this final blend may then be compressed on a conventional tablet press.

In producing a capsule solid-dosage form, the mixed and blended material may be introduced into each capsule by appropriate, automated equipment. If a capsule is to be produced the coloring agent may be eliminated and the upper limit of granule size, may be such that not more than 5% exceeds 1.5 mm in length.

Desirably, a unit-dosage form may be a 0.4 gram tablet, as made by the above method. This tablet would contain from the first mixture about 75 milligrams of triamterene, U.S.P., 38 milligrams of wicking agent, 125 milligrams of a binder-disintegrant, 10 milligrams of a disintegrant, 4 milligrams of a wetting agent or surfactant such as sodium lauryl sulfate, U.S.P., 6 milligrams of magnesium stearate/sodium lauryl sulfate (94/6) and 2 milligrams of a flow enhancer; and will further contain, from the second mixture, 50 milligrams of hydrochlorothiazide, U.S.P., 80 milligrams of a binder-disintegrant, 5 milligrams of a disintegrant, 1 milligram of a flow enhancer, 1 milligram of magnesium stearate/sodium lauryl sulfate (94/6) and 1 milligram of a coloring agent. In addition, 2 milligrams of magnesium stearate/sodium lauryl sulfate (94/6) will be present, as introduced in the final blending operation.

A preferred tablet formulation, consisting of 50 mg hydrochlorothiazide and 75 mg triamterene in the tablet, made up according to the foregoing procedure, uses the following materials in the indicated amounts.

| Component | Amount | Mg per Tablet |
|---|---|---|
| First Mixture | | |
| Triamterene | 9.38 Kg | 75 |
| Avicel, PH-102 | 15.6 Kg | 125 |
| Rexcel | 4.75 Kg | 38 |
| Ac-Di-Sol | 1.25 Kg | 10 |
| Magnesium Stearate/Sodium Lauryl Sulfate (94/6) | 750 g | 6 |
| Sodium Lauryl Sulfate, N.F. | 500 g | 4 |
| Cab-O-Sil, M-5 | 250 g | 2 |
| Second Mixture | | |
| Hydrochlorothiazide | 6.25 Kg | 50 |
| Avicel, PH-102 | 10.0 Kg | 80 |
| Ac-Di-Sol | 625 g | 5 |
| Magnesium Stearate/Sodium Lauryl Sulfate (94/6) | 125 g | 1 |
| Cab-O-Sil, M-5 | 125 g | 1 |
| D & C Yellow #10 Lake HT (17–20%) | 125 g | 1 |

After the separate granules were prepared, 250 g of magnesium stearate/sodium lauryl sulfate (94/6) were added and the final mixture thoroughly blended and then formed into tablets (or capsules) by customary methods.

EXAMPLE 1-A

A second tablet formulation, containing 50 mg hydrochlorothiazide and 100 mg triamterene in the tablet, was made up according to the foregoing procedure, using the following materials in the indicated amounts.

| Component | Amount | Mg per Tablet |
|---|---|---|
| First Mixture | | |
| Triamterene | 10.0 Kg | 100 |
| Avicel, PH-102 | 18.5 Kg | 185 |
| Rexcel | 5.00 Kg | 50 |
| Ac-Di-Sol | 1.60 Kg | 16 |
| Magnesium Stearate/Sodium Lauryl Sulfate (94/6) | 800 g | 8 |
| Sodium Lauryl Sulfate, N.F. | 500 g | 5 |
| Cab-O-Sil, M-5 | 400 g | 4 |
| Second Mixture | | |
| Hydrochlorothiazide | 5.00 Kg | 50 |
| Avicel, PH-102 | 10.0 Kg | 100 |
| Ac-Di-Sol | 600 g | 6 |
| Magnesium Stearate/Sodium Lauryl Sulfate (94/6) | 100 g | 1 |
| Cab-O-Sil, M-5 | 100 g | 1 |
| D & C Yellow #10 Lake HT (17–20%) | 100 g | 1 |

After the separate granules were prepared, 300 g of magnesium stearate/sodium lauryl sulfate (94/6) were added and the same blended and then formed into tablets or capsules as above.

EXAMPLE 1-B

A capsule formulation, containing 25 mg hydrochlorothiazide and 50 mg triamterene in the capsule, was made up according to the foregoing procedure, using the following materials in the indicated amounts.

| Component | Amount | Mg per Capsule |
|---|---|---|
| First Mixture | | |
| Triamterene | 10.0 Kg | 50 |
| Rexcel | 4.00 Kg | 20 |
| Avicel, Ph-102 | 2.40 Kg | 12 |
| Ac-Di-Sol | 600 g | 3 |
| Sodium Lauryl Sulfate, N.F. | 600 g | 3 |
| Magnesium Stearate/Sodium Lauryl Sulfate (94/6) | 300 g | 1.5 |
| Cab-O-Sil, M-5 | 100 g | 0.5 |
| Second Mixture | | |
| Hydrochlorothiazide | 5.00 Kg | 25 |
| Avicel, PH-102 | 8.00 Kg | 40 |
| Ac-Di-Sol | 600 g | 3 |
| Cab-O-Sil, M-5 | 100 g | 0.5 |
| Magnesium Stearate/Sodium Lauryl Sulfate (94/6) | 100 g | 0.5 |

After the seperate granules were prepared, 200 g of magnesium stearate/sodium lauryl sulfate (94/6) were added to the same and blended, and then formed into No. 4 capsules by conventional methods.

EXAMPLE 2

In order to determine the bioavailability of the composition of the present invention as compared with a prior, currently-marketed, composition formed of an intimate admixture of hydrochlorothiazide and triamterene, and with a suspension which latter serves as an optimally bioavailable reference standard, the following tests were performed.

An aqueous suspension containing 100 mg of triamterene and 50 mg of hydrochlorothiazide was administered to six healthy volunteers. At a different time these participants were given a single tablet (containing 75 mg of triamterene and 50 mg of hydrochlorothiazide) formed according to this invention. Other participants were given two prior art presently-marketed capsules (containing a combined total of 100 mg triamterene/50 mg hydrochlorothiazide; the only previously FDA-approved triamterene/hydrochlorothiazide combination formulation). Following each dosing, urine was collected and the amounts of drug recovered were quantified. A summary of the triamterene urinary recovery results (in mg recovered in urine during a 72 hour period after dosing) is presented in Table I.

TABLE I

| TRIAMTERENE BIOAVAILABILITY* | | | |
|---|---|---|---|
| PARTICIPANT | SUSPEN-SION** (100/50) | PRIOR ART** (50/25 CAPSULE) | PRESENT INVENTION*** (75/50 TABLET) |
| 1 | 61.2 | 28.3 | 45.5 |
| 2 | 50.6 | 28.5 | 49.4 |
| 3 | 42.2 | 18.6 | 39.5 |
| 4 | 55.9 | 20.8 | 36.2 |
| 5 | 64.5 | 21.5 | 36.9 |
| 6 | 49.9 | 23.2 | 34.7 |
| Mean | 54.1 | 23.5 | 40.4 |
| Std. Dev. | 8.2 | 4.1 | 5.8 |
| C.V. | 15.1 | 17.0 | 14.0 |
| % Dose | 54.1 | 23.5 | 53.9 |

*Represents total triamterene plus hydroxy triamterene sulfate ester. (The conjugate results from triamterene being metabolized in the liver.)
**Total Dose = 100 mg triamterene; 50 mg hydrochlorothiazide.
***Total Dose = 75 mg triamterene; 50 mg hydrochlorothiazide.

These tests resulted in a mean triamterene biovailability of 53.9% of the dose administered for the compound of this invention, comparable to the value of 54.1% for the suspension, as contrasted with a mean of only 23.5% for the prior art capsule.

Later a second test was performed, again with the first group of six healthy volunteer participants, using the prior art capsules and capsules formulated according to the present invention (Example 1-B). The resulting data, similarly measured is presented in Table I-A (along with certain data from Table I for convenient comparison).

TABLE IA

| TRIAMTERENE BIOAVAILABILITY | | | | |
|---|---|---|---|---|
| PARTIC-IPANT | SUS-PEN-SION* | PRIOR ART (50/25 CAPSULE)* | PRESENT INVEN-TION (50/25 CAPSULE)* | PRESENT INVEN-TION (75/50 TABLET)** |
| 1 | 61.2 | 16.3 | 45.5 | 45.5 |
| 2 | 50.6 | 26.8 | 44.9 | 49.4 |
| 3 | 42.2 | 20.1 | 34.4 | 39.5 |
| 4 | 55.9 | 45.9 | 33.1 | 36.2 |
| 5 | 64.5 | 20.4 | 31.6 | 36.9 |
| 6 | 49.9 | 23.4 | 40.1 | 34.7 |
| Mean | 54.1 | 25.5 | 38.3 | 40.4 |
| Std Dev | 8.2 | 10.6 | 6.1 | 5.8 |
| C.V. | 15.1 | 41.0 | 16.0 | 14.0 |
| Mean % Dose | 54.1 | 25.5 | 38.3 | 53.9 |

*Dose Administered: 100 mg Triamterene/50 mg Hydrochlorothiazide
**Dose Administered: 75 mg Triamterene/50 mg Hydrochlorothiazide A similar summary of the hydrochlorothiazide urinary recovery results (in mg recovered in urine during a 72 hour period after dosing) corresponding respectively to Tables I and I-A, is presented in Tables II and II-A.

TABLE II

| HYDROCHLOROTHIAZIDE BIOAVAILABILITY | | | |
|---|---|---|---|
| PARTICIPANT | SUSPEN-SION* (100/50) | PRIOR ART* (50/25 CAPSULE) | PRESENT INVENTION (75/50 TABLET)** |
| 1 | 31.5 | 24.2 | 29.5 |
| 2 | 29.7 | 15.8 | 26.9 |
| 3 | 24.6 | 25.6 | 31.7 |
| 4 | 26.4 | 21.6 | 24.9 |
| 5 | 33.1 | 11.3 | 31.1 |
| 6 | 32.8 | 15.8 | 38.4 |
| Mean | 29.7 | 19.1 | 30.4 |
| Std. Dev. | 3.5 | 5.6 | 4.7 |
| C.V. | 11.8 | 29.0 | 15.0 |
| Mean % Dose | 59.4 | 38.0 | 60.8 |

*Total Dose = 100 mg Triamterene; 50 mg Hydrochlorothiazide.
**Total Dose = 75 mg Triamterene; 50 mg Hydrochlorothiazide.

The mean % hydrochlorothiazide bioavailability in Table II was 60.8% for the present (tablet) composition which is close to the 59.4% value of the suspension, as contrasted with only 38.0% for the prior art.

In Table II-A the mean availability of hydrochlorothiazide was only 30.8% of the dose administered with the prior art capsule, whereas the present capsule had a mean bioavailability of 51.6%, and for the present tablet of 60.8%.

TABLE II-A

| HYDROCHLOROTHIAZIDE BIOAVAILABILITY | | | | |
|---|---|---|---|---|
| PARTIC-IPANT | SUS-PEN-SION* | PRIOR ART* (50/25 CAPSULE) | PRESENT INVEN-TION* (50/25 CAPSULE) | PRESENT INVEN-TION** (75/50 TABLET) |
| 1 | 31.5 | 10.3 | 28.6 | 29.5 |
| 2 | 29.7 | 11.4 | 28.5 | 26.9 |

TABLE II-A-continued

| | | | PRESENT | PRESENT |
| | | | INVEN- | INVEN- |
| | SUS- | PRIOR ART* | TION* | TION** |
| PARTIC- | PEN- | (50/25 | (50/25 | (75/50 |
| IPANT | SION* | CAPSULE) | CAPSULE) | TABLET) |
|---|---|---|---|---|
| 3 | 24.6 | 14.3 | 24.5 | 31.7 |
| 4 | 26.4 | 23.3 | 16.3 | 24.9 |
| 5 | 33.1 | 17.8 | 32.5 | 31.1 |
| 6 | 32.8 | 15.2 | 24.4 | 38.4 |
| Mean | 29.7 | 15.4 | 25.8 | 30.4 |
| Std. Dev. | 3.5 | 4.7 | 5.6 | 4.7 |
| C.V. | 11.8 | 31.0 | 22.0 | 15.0 |
| % Dose | 59.4 | 30.8 | 51.6 | 60.8 |

HYDROCHLOROTHIAZIDE BIOAVAILABILITY

*Dose Administered: 100 mg Triamterene/50 mg Hydrochlorothiazide
**Dose Administered: 75 mg Triamterene/50 mg Hydrochlorothiazide Thus a significantly higher percentage of both active ingredients was available from the composition made according to this invention than from the prior art product.

In still another test the same first set of six volunteer participants (see Example 2 above) were treated with a tablet made using the technique according to this invention (Example 1-A, above) but containing 100 mg triamterene and 50 mg hydrochlorothiazide. The results, measured in the same manner as in Tables I, IA, II and II-A, are shown in Table III.

TABLE III
TRIAMTERENE PLUS HYDROCHLOROTHIAZIDE TABLETS (100 mg/50 mg)

| PARTICIPANT # | TRIAMTERENE | HYDROCHLORO-THIAZIDE |
|---|---|---|
| 1 | 53.6 | 30.2 |
| 2 | 65.5 | 36.6 |
| 3 | 42.5 | 31.2 |
| 4 | 32.3 | 31.7 |
| 5 | 53.5 | 26.9 |
| 6 | 40.8 | 30.1 |
| Mean | 48.0 | 31.1 |
| Std Dev | 11.8 | 3.2 |
| C.V. | 24.6 | 10.3 |
| % Dose | 48.0 | 62.2 |

These results indicate a mean level of bioavailability and absorption for triamterene for this tablet (48 mg from 100 mg) exceeding by some 25% what has been thought to be the limit in absorptive capacity of the gastrointestinal tract of about a mean of 39% from an administration of 100 mg, as reported in independent tests with differently formulated compositions; see Tannenbaum et al, Clinical Pharmacology and Therapeutics, Vol. 5, No. 9, pp. 598–604 (1968).

Further this example illustrates the effectiveness of the present invention in a tablet with a ratio of triamterene:hydrochlorothiazide of 2:1 (as also with the capsules in Tables I-A and II-A); however, for clinical reasons a ratio in the range of 1.75 to 1.25:1 is more advantageously used.

It will also be seen from the foregoing tables that compositions formulated according to the present invention exhibit a high level of uniformity of response as evidenced by this relative low coefficient of variation (C.V.) figures (comparable to those shown by administering the same ingredients in suspension form). Moreover, an adequate triamterene (and hydrochlorothiazide) level is made available by administering a single (e.g. 75/50) tablet, without need to resort to a multiple tablet prescription, and with the total administered relative amount of triamterene being less than has been employed in the past.

EXAMPLE 3

Other tests were performed to determine the triamterene dose response characteristics in hypertensive individuals who had become hypokalemic (serum K+ 2.9–3.5 mEq/L) under treatment with hydrochlorothiazide, 50 mg/day. In an effort to determine the minimum amount of triamterene needed to reverse the hypokalemia precipitated by hydrochlorothiazide, each subject was continued on hydrochlorothiazide, 50 mg/day administered in a separate tablet, and was also given one of the following daily dosages of triamterene, administered in suspension form throughout the testing period: 0 mg, 25 mg, 50 mg, 75 mg, and 100 mg. The average serum potassium reading in mEq/L are shown in Table IV, with each grouping of readings representing a given dosage level.

TABLE IV

| Dose (mg) | Mean Serum K+ before Triamterene* | Mean Serum K+ after Triamterene** |
|---|---|---|
| 100 | 3.58 | 3.58 |
| 100 | 3.22 | 3.77 |
| 100 | 3.42 | 3.76 |
| 100 | 3.30 | 3.90 |
| 100 | 3.15 | 3.78 |
| 100 | 3.47 | 3.55 |
| 100 | 3.48 | 3.83 |
| 100 | 3.53 | 3.90 |
| 100 | 3.21 | 4.03 |
| 75 | 3.57 | 3.73 |
| 75 | 3.57 | 4.03 |
| 75 | 3.47 | 4.17 |
| 75 | 3.28 | 3.25 |
| 75 | 3.53 | 3.48 |
| 75 | 3.50 | 4.00 |
| 75 | 3.58 | 4.28 |
| 75 | 3.25 | 3.72 |
| 75 | 3.10 | 3.50 |
| 75 | 3.10 | 3.73 |
| 50 | 3.15 | 3.26 |
| 50 | 3.13 | 3.27 |
| 50 | 3.63 | 3.67 |
| 50 | 3.50 | 4.43 |
| 50 | 3.48 | 3.73 |
| 50 | 3.43 | 3.89 |
| 50 | 3.57 | 3.75 |
| 50 | 3.53 | 3.78 |
| 50 | 3.58 | 4.15 |
| 50 | 3.63 | 3.87 |
| 25 | 3.36 | 3.73 |
| 25 | 3.60 | 3.71 |
| 25 | 3.56 | 3.40 |
| 25 | 3.25 | 3.15 |
| 25 | 3.61 | 3.56 |
| 25 | 3.15 | 3.36 |
| 25 | 3.50 | 3.33 |
| 25 | 3.36 | 3.51 |
| 25 | 3.60 | 3.71 |
| 0 (placebo) | 3.43 | 3.40 |
| 0 | 3.67 | 3.75 |
| 0 | 3.48 | 3.22 |
| 0 | 3.38 | 3.48 |
| 0 | 3.32 | 3.37 |
| 0 | 3.23 | 3.22 |
| 0 | 3.58 | 3.43 |

*Represents an average of 6 baseline measurements taken over two weeks.
**Represents an average of 6 measurements taken over two weeks.

These data confirm the effectiveness of optimally bioavailable triamterene for reversing hydrochlorothiazide-induced hypokalemia. The effectiveness was particularly large in the upper ranges of the doses tested. At a dosage level of about 75 mg triamterene (with 50 mg hydrochlorothiazide), a near maximal response is seen.

By comparison of these results with the data shown in Table I and I-A, it will be seen that the presently-marketed prior art composition fails to provide an adequate biavailability of triamterene for the correction or reversal of a hypokalemic condition, in contrast to the levels provided by the compositions of the present invention.

EXAMPLE 4

To further confirm the enhanced, optimal, bioavailability of the respective active ingredients of the compositions provided by this invention, tablets were formulated according to this invention containing 75 mg of triamterene and 50 mg of hydrochlorothiazide. Dissolution rate studies were then performed on these tablets using USP Paddle Method in 900 ml. of artificial gastric fluid without enzymes, pH 1.2, at 37° C. and at 50 RPM. This test is described under Dissolution, Method II of the 4th Supplement, United States Pharmacopeia XIX, National Formulary XIV, page 194, released Jan. 31, 1978; such dissolution results have been utilized by the Food and Drug Administration for triamterene-hydrochlorothiazide combination products (V. P. Shah, F. K. Prasad, J. Lin, G. Knapp, and B. E. Cabana, Biopharmaceutics Laboratory, in a recent paper delivered at the National Meeting of the American Pharmaceutical Association, Academy of Pharmaceutical Sciences Division, Nov. 14–18, 1982). The results of this test after 30 minutes and 60 minutes are reported in Table V. For comparison, dissolution results obtained with the prior art presently marketed (50/25) capsule are also included in Table V. It will be noted that both the triamterene dissolution and the hydrochlorothiazide dissolution rates are very high for the product made by the present invention.

TABLE V

DISSOLUTION DATA* (%)

| | Present Invention (Tablet) | | Prior Art (Capsule) | |
|---|---|---|---|---|
| | Hydrochlorothiazide | Triamterene | Hydrochlorothiazide | Triamterene |
| 30 min | 83.1  80.1 | 82.7  89.0 | 6.9  7.1 | 5.5  5.6 |
|  | 84.3  79.1 | 87.0  79.7 | 3.9  7.2 | 3.9  5.4 |
|  | 100.7  89.9 | 90.9  89.5 | 4.1  9.0 | 4.0  8.2 |
|  | 98.1  91.7 | 88.9  86.4 | 4.1  8.1 | 4.1  6.5 |
|  | 100.6  78.8 | 93.1  87.7 | 3.7  7.7 | 4.2  6.0 |
|  | 99.2  88.3 | 90.5  88.2 | 4.2  7.6 | 3.7  5.7 |
| Mean | 89.5 | 87.8 | 6.1 | 5.3 |
| Std. Dev. | 8.5 | 3.6 | 2.0 | 1.2 |
| C.V. | 9.5 | 4.1 | 32.8 | 25.0 |
| 60 min | 86.0  87.1 | 86.9  96.3 | 15.3  14.0 | 12.0  10.3 |
|  | 90.7  87.3 | 92.1  87.3 | 13.0  14.8 | 10.1  10.9 |
|  | 103.9  97.0 | 94.9  95.9 | 12.7  17.3 | 10.5  11.8 |
|  | 100.5  96.4 | 92.4  91.3 | 13.4  16.0 | 12.2  16.0 |
|  | 105.7  85.6 | 98.6  96.3 | 14.1  14.9 | 13.1  12.3 |
|  | 100.4  91.6 | 91.4  92.7 | 13.3  15.1 | 12.5  10.2 |
| Mean | 94.3 | 93.0 | 14.5 | 11.8 |
| Std. Dev. | 7.2 | 3.6 | 1.3 | 1.7 |
| C.V. | 7.6 | 3.9 | 9.0 | 14.4 |

*USP XX Method II 50 rpm
900 ml pH 1.2 Gastric Fluid (0.1N HCl) Without Enzymes

Thus, even though the problem of formulating hydrochlorothiazide and triamterene together in a solid unit dosage form of enhanced bio-effectiveness has been recognized and is of longstanding, the advance and contribution provided by the present invention has escaped discovery by skilled workers in the field prior to the present invention.

It will be appreciated, therefore, that the present invention provides a unique method for manufacturing a non-toxic pharmaceutical combination composition which provides effective diuretic and antihypertensive properties while resisting or reversing undesired hydrochlorothiazide-induced hypokalemic action and minimizing the amount of triamterene which must be employed. All of this is accomplished while producing bioavailability substantially equal to or even better than single entity dosage of hydrochlorothiazide, or of triamterene.

In administering such an embodiment of the present invention, a patient will typically be given the composition in daily dosages such that the total triamterene consumed per day need not be greater than the desired ceiling of about 150 milligrams per day. Daily dosages of triamterene will generally be about 37 to 150 milligrams.

While the foregoing examples have illustrated the practice of the invention with the preferred hydrochlorothiazide and triamterene ingredients, it will be understood that the same procedures may be followed with alternative ingredients. Thus, in place of triamterene, there may be used 2,4,7-triamino-6-p-fluorophenylpteridine, 2,4,7-triamino-6-p-trifluoromethyl-phenylpteridine, 2,4,7-triamino-6-p-ethoxyphenylpteridine, 7-dimethylamino-2,4-bismethylamino-6-phenylpteridine, 2,4,7-triamino-6-α-thienylpteridine, 2,47-triamino-6-o-methylphenylpteridine, 4,7-diamino-2-dimethylamino-6-phenylpteridine, 2,4,7-triamino-6-m-methoxyphenylpteridine, 2,4,7-triamino-6-o-methylphenylpteridine. Metabolic products of triamterene and such other pteridine may also be employed, such as the hydroxy triamterene sulfuric acid ester. It will be understood that as used herein the phrase "a triamterene-active pteridine ingredient" refers to one or more of such components.

Further, in place of hydrochlorothiazide, there may instead be used chlorothiazide, benzydroflumethiazide, trichloromethiazide, hydroflumethiazide, flumethiazide, methyclothiazide, chlorthalidone, or benzthiazide. It will be understood that as used herein the phrase "a hydrochlorothiazide-active benzothiadiazide ingredient" referes to one or more of these compounds.

More broadly, this invention also provides a general technique for the formulation of solid medicinal compositions containing at least two pharmaceutically active ingredients, at least one of which is relatively hydrophobic with respect to the other(s), wherein the bioavailability of each of the active ingredients, when in the combination, is enhanced. That is, combinations of active ingredients other than as specifically mentioned above may also be employed, utilizing the same basic procedures, this invention having particular utility where one of such ingredients is relatively hydrophobic with respect to the other, but where a high level of bioavailability is desired for both. In general, in such compositions, the appropriate weight ratio of such pharmaceutically active ingredients will be chosen for maximal effectiveness of the respective active ingredients by straight-forward clinical and laboratory tests, e.g. as described above, or other appropriate tests as will be selected by those skilled in the art.

Whereas particular embodiments of the invention have been described above for purposes of illustration, it will accordingly be evident to those skilled in the art that numerous variations of the details may be made without departing from the invention as defined in the following claims.

What is claimed is:

1. A method of administering a solid antihypertensive diuretic medication to a patient composed of at least one hydrochlorothiazide-active thiazide ingredient and at least one triamterene-active pteridine ingredient which effectively inhibits and/or reverses benzothiadiazide-induced hypokalemia, and which consists essentially in forming a solid unit dose composition composed of, as active ingredients, finely-divided particles of said benzothiadiazine ingredient which has been first separately admixed with at least one finely-divided pharmaceutically acingredient, and finely-divided particles of said pteridine ingredient, which had been first separately admixed with at least one finely-divided pharmaceutically-acceptable ingredient including a non-toxic pharmaceutically acceptable inert carrier materials of the class including wicking agents, surfactants, disintegrants, lubricants, and compacting aids with said relatively hydrophobic pteridine ingredient particles being substantially isolated from direct content with said benzothiadiazide ingredient particles in said composition, and said composition exhibiting a sufficiently enhanced bioavailability of said pteridine ingredient, with respect to the bioavailability thereof in a solid composition having said finely divided active ingredients present in intimate admixture with each other, such that benzothiadiazide-induced hypokalemia is effectively resisted or reversed, at dose levels of said benzothiadiazide ingredient effective for antiphypertensive and diuretic control, and administering said composition orally to said patient.

2. A method according to claim 1 wherein said unit dose composition is formulated as a capsule.

3. A method according to claim 1 wherein said unit dose composition is formulated as a tablet, said tablet containing an additional lubricant blended in with said active ingredients in the formulation of said tablet.

4. A method according to claim 1 wherein said respective finely-divided particles of each of said respective active ingredients is first separately blended together with said inert carrier materials, and separately compacted, after which they are respectively separately comminuted to form respective granules which are thereafter blended to form the combination composition.

5. A method according to claim 1 wherein said benzothiadiazide ingredient is hydrochlorothiazide and said pteridine ingredient is triamterene at a weight ratio of triamterene to hydrochlorothiazide of from 1.25 to 1.75:1.

6. A method according to claim 5 wherein said weight ratio is 1.5:1.

7. A granularly-heterogenous composition having combined pharmaceutically-effective antihypertensive, diuretic and antihypokalemic properties composed of (a) discrete, separately formed first granules containing finely-divided particles of a triamterene active pteridine ingredient admixed with at least one finely-divided pharmaceutically-acceptable inert ingredient, and (b) discrete, separately formed second granules containing finely-divided particles of a hydrochlorothiazide active benzothiadiazine ingredient admixed with at least one finely-divided pharmaceutically-inactive inert ingredient, with said first and second granules being admixed and blended together in amounts such that the resulting blended composition has a weight ratio of said pteridine ingredient to said benzothiadiazine ingredient provides an effective bioavailability of said pteridine to control the hypokalemic condition induced by the dosage amount of said benzothiadiazide.

8. A composition according to claim 7 wherein said finely-divided pharmaceutically inactive inert ingredients are of the class including wicking agents, disintegrants, surfactants, lubricants and compacting aids.

9. A composition according to claim 8 wherein said pteridine ingredient is triamterene and said benzothiadiazide ingredient is hydrochlorothiazide.

10. A composition according to claim 9 wherein said weight ratio is about 1.5:1.

11. A composition according to claim 7 formulated as a unit dosage capsule.

12. A composition according to claim 7 formulated as a unit dosage tablet, which includes at least one lubricant blended with said first and second granules.

* * * * *

UNITED STATES PATENT AND TRADEMARK OFFICE
CERTIFICATE OF CORRECTION

PATENT NO. : 4,444,769
DATED : April 24, 1984
INVENTOR(S) : Cheryl D. Blume et al.

It is certified that error appears in the above-identified patent and that said Letters Patent is hereby corrected as shown below:

Column 1, Line 38, after "other" insert --or--.
Column 3, Line 38, "whth" should read --with--.
Column 4, Line 42, after "amount" insert a comma --,--; after "basic" insert a comma --,--.
Column 5, Line 2, before "dodecyl" cancel the bracket "[" and insert --(--; Line 3, after the formula insert --)--; Line 29, after "salt" insert a comma --,--; also in Line 29, "mg" should read --Mg--; and Line 35, after "N.F." insert --($SiO_2$)--.
Column 11, first line after the first table, change "seperate" to --separate--; Line 61, in TABLE I, before "% Dose" insert --Mean--.
Column 12, Line 15 in TABLE IA, after "SUSPENSION" insert --(100/50)--; at Line 25, after "Mean" insert --% Dose--; Line 26, delete "% Dose"; Line 66, in TABLE II-A, after "SUSPENSION" insert --(100/50)--.
Column 14, Line 7, change "3.5 mEq/L" to --3.6 mEq/L--.

UNITED STATES PATENT AND TRADEMARK OFFICE
CERTIFICATE OF CORRECTION

PATENT NO. : 4,444,769

DATED : April 24, 1984

INVENTOR(S) : Cheryl D. Blume et al.

It is certified that error appears in the above-identified patent and that said Letters Patent is hereby corrected as shown below:

Column 17, Line 13, "acingredient" should read --acceptable ingredient--; Line 33, correct the spelling of --antihypertensive--.

Column 18, Line 24, "inactive" should read --acceptable--. --acceptable--.

Signed and Sealed this

Thirtieth Day of April 1985

[SEAL]

Attest:

DONALD J. QUIGG

Attesting Officer

Acting Commissioner of Patents and Trademarks